United States Patent [19]

Coffey et al.

[11] Patent Number: 5,314,691
[45] Date of Patent: May 24, 1994

[54] **BIOLOGICAL CONTROL OF PHYTOPHTHORA ON PLANTS AND IN SOIL WITH *MYROTHECIUM RORIDUM* ATCC 20963, 20964 OR 20965**

[75] Inventors: Michael D. Coffey, Riverside, Calif.; René Gees, Schönenbuch, Switzerland

[73] Assignee: The Regents of the University of California, Oakland, Calif.

[21] Appl. No.: 898,222

[22] Filed: Jun. 12, 1992

Related U.S. Application Data

[63] Continuation of Ser. No. 434,701, Nov. 9, 1989, abandoned.

[51] Int. Cl.$^5$ ................. A01N 63/00; C12N 1/14
[52] U.S. Cl. ................. 424/93 Q; 435/254.1; 435/911
[58] Field of Search ............. 424/93 R, 93 Q; 435/252.1, 254.1, 911

[56] References Cited

U.S. PATENT DOCUMENTS

| | | | |
|---|---|---|---|
| 4,382,952 | 5/1983 | Bloem et al. | 435/119 X |
| 4,463,182 | 7/1984 | Freckman | 549/264 |
| 4,996,157 | 2/1991 | Smith et al. | 424/93 X |

OTHER PUBLICATIONS

Munnecke, D. E., Trans. Br. Mycol. Soc. 83(2), 1984, pp. 287–294.
Nespiak, A., et al., "Antibiotic Properties of Mycelium and Metabolites of Myrothecium Roridum Tode", *Nature*, Oct. 14, 1961, vol. 192, pp. 138–139.
Brian, P. W., et al., "Production of Antibiotics by Species of Myothecium", *Mycologia*, 1948, vol. 40, pp. 363–368.
Suryanarayana, K., et al., "Effect of Metabolites of Myrothecium Leucotrichum on the Germination of Spores of Plant Pathogenic Fungi", *Current Sciences*, Jun. 5, 1980, vol. 49, No. 11, pp. 442–444.
Reyes, A., et al., "Suppression of Fusarium and Pythium pea root rot by antagonistic microorganisms", *Phytoprotection*, Jan. 30, 1984, vol. 66, pp. 23–29.
Mishra, R. R., et al., "Studies on Biological Control of Puccinia Graminis Tritici", *Microbiology of Aerial Plant Surfaces*, 1976, (C. H. Dickenson and T. F. Preece, Editors), pp. 559–567, Academic Press, New York.
Abstract of Conference on Phytophthora diseases of citrus and other crops in the Mediterranean area, held at Palermo (IT), Apr. 18–22, 1989.
Appel, D. J., Abstract of the Thesis, "Biological Control of Penicillium digitatum on Lemon Fruit Using Fungal Antagonists", University of California, Riverside, Mar., 1989.
Gees, R., et al., Abstracts of Presentations at the 1988 Annual Meeting of the American Phytopathological Society and the Pacific Division, Nov. 13–17, 1988, San Diego, Calif., "A Strain of Myrothecium as a Potential Biocontrol Agent Against Phytophthora Cinnamomi", University of California, Riverside.

(List continued on next page.)

*Primary Examiner*—David M. Naff
*Attorney, Agent, or Firm*—Townsend and Townsend Khourie and Crew

[57] ABSTRACT

Plant pathogenic fungi belonging to the genus Phytophthora such as *phytophthora cinnamomi* which causes root rot in plants is biologically controlled with strains of fungi belonging to the genus Myrothecium. Preferred strains of Myrothecium are *Myrothecium roridum* ATCC 20963, 20964 or 20965. An inoculum containing Myrothecium and a substrate such as bran or a branalginate mixture is added to the surface of a plant or to soil. The Myrothecium may be grown on the substrate 5 to 7 days before use of the inoculum.

22 Claims, 2 Drawing Sheets

OTHER PUBLICATIONS

Appel, D. J., Abstracts of Presentations at the 1988 Annual Meeting of the American Phytopathological Society and the Pacific Divisioin, Nov. 13 17, 1988, San Diego, Calif., "Biological Control of the Postharvest Pathogen Penicillium Digitatum on Eureka Lemons", University of California, Riverside.

Ahmad, J. S., et al., Abstract, "Competitive Saprophytic Abiblity and Cellulolytic Activity of Rhizosphere-Competent Mutants of Trichoderma harzianum", Jul. 25, 1986, *Phytopathology*, vol. 77, pp. 358–362.

Thode, R., Thesis for Master of Science, "Fusarium solani, Fusarium equiseti and Myrothecium verrucaria as Parasites of Pythium ultimum", University of California, Davis, 1977.

Ferguson, J., Doctoral Thesis, "Reducing Plant Diseases with Fungicidal Soil Treatment, Pathogen-Free Stock, and Controlled Microbial Colonization", Deposited in the University Library Mar. 3, 1959, University of California.

Gees, R., et al., Abstract, "Evaluation of a Strain of Myrothecium roridum as a Potential Agent against Phytophthora cinnamomi", *Phytopathol*, vol. 79, pp. 1079–1084, 1989.

BIOLOGICAL CONTROL OF PHYTOPHTHORA ON PLANTS AND IN SOIL WITH *MYROTHECIUM RORIDUM* ATCC 20963, 20964 OR 20965

This application is a continuation of application Ser. No. 07/434,701, filed Nov. 9, 1989, now abandoned.

FIELD OF THE INVENTION

This invention relates to a method for biological control of plant pathogenic fungi in soil and on plant surfaces, and more particularly to the use of the fungi, belonging to the genus Myrothecium, to control and suppress the organism Phytophthora in plants. The invention also relates to new strains of Myrothecium useful in biological control.

BACKGROUND OF THE INVENTION

Soilborne plant diseases present an ongoing challenge to the plant pathologist. Plant pathogenic fungi cause severe economic losses throughout the world on many plant crops. For example, root rot of avocado (*Persea americana* Mill.) caused by *Phytophthora cinnamomi* Rands, is the major disease affecting avocado trees in California (Coffey, "Phytophthora root rot of avocado: an integrated approach to control in California" *Plant Dis.* 71:1046–1052 (1987)). Only two fungicides (metalaxyl and fosetyl-Al) are available that are only partially effective in suppressing the pathogen under conditions present in California (Cohen and Coffey, "Systemic fungicides and the control of oomycetes", *Ann. Rev. Phytopathol.* 24:311–338, (1986)). Total dependence on such site-specific fungicides is not recommended, because, aside from their high cost, fungicide-resistant strains of *P. cinnamomi* may occur through their excessive use (Cohen and Coffey, supra).

Another example is citrus postharvest disease caused by *Penicillium digitatum. P. digitatum* is a major source of decay of citrus fruit shipped from California and the Mediterranean region. This pathogen has developed fungicide resistance (Eckert and Brown, "Postharvest citrus diseases and their control" in "Fresh Citrus Fruits", Wardowski et al., Eds., pp. 315–361 (1986b)), rendering traditional methods of control ineffective.

An urgent need exists for an effective, broad-based, integrated approach to the management of such plant diseases. Traditional methods of control such as breeding for resistance, crop rotation and the use of chemical pesticides have been relatively unsuccessful and economically impractical.

"Biological control" involves the control of one organism by another antagonistic organism, defined as a biological agent with the potential to interfere in the life processes of plant pathogens. In the present invention "biological control" means the use of an organism to reduce the amount of inoculum or disease-producing ability of a plant pathogen. Mechanisms of biological control include 1) antibiosis, defined as the inhibition or destruction of the disease-causing organism by a metabolic product or products of the control organism, both specific and non-specific in nature, and including lytic agents, enzymes, volatile compounds or other toxic compounds, 2) competition, in which the introduced control organism successfully outcompetes the disease-causing organism for food and/or space, and 3) parasitism, in which the control organism parasitizes the disease-causing organism. Biological control may be accomplished by habitat management, for example to create an environment that favors organisms that are antagonistic to the pathogen; creation of host plant resistance to the pathogen; or by introduction of antagonists, or nonpathogenic strains. The term "biological control" as used herein may include antibiotic production and the effects of such production by the antagonistic organism in the suppression of the plant pathogen, however, the term as used herein includes the broader action of an antagonist in suppression beyond antibiotic production. Thus, demonstration of antibiotic production in vitro does not necessarily predict the ability of an organism to biologically control a plant pathogen in vivo, i.e. the ability to suppress infection by the pathogen of host plants present in soil. An antagonistic organism introduced into soil "in the field" must compete with other organisms and conditions present in the soil and on plant surfaces, including roots, stems, leaves and fruit to be effective in suppression of the pathogen. Antibiotic production alone may not be sufficient to cause suppression of the pathogen in the soil around the plant. Antibiosis often acts in concert with competition and/or parasitism. Therefore, the presence or absence of antibiotic production is not determinative of the ability of an organism to function as a biological control agent against a plant pathogen in soil (Fravel, "Role of Antibiosis in the Biocontrol of Plant Diseases", *Ann. Rev. of Phytopathology* 26:75–91 (1988)).

Attempts to use organisms such as bacteria and fungi to control plant diseases have been described. For example, Mishra et al. described the use of bacteria to control rust disease of wheat caused by *Puccinia qraminis tritici* (Mishra and Tewari, in "Microbiology of Aerial Plant Surfaces", Dickinson and Preece, eds., pp. 559–567, Academic Press, New York (1976).

Suppressive soils are defined as soils in which disease is minimal or diminishing even in the presence of susceptible host tissue, with or without reduction of the pathogen population. (Malajczuk, "Microbial antagonism to Phytophthora" in Phytophthora: Its Biology, Taxonomy, Ecology and Pathology, Erwin et al., Eds., Ch. 16 (1983)). Through introduction of single antagonistic organisms, repeated attempts have been made to enhance the suppressive effects of soils against specific plant pathogens (Ferguson, "Reducing plant disease with fungicidal soil treatment, pathogen free stock, and controlled microbial colonization", Ph.D. thesis, University of California, Berkeley (1958); Hadar et al., "Biological control of *Rhizoctonia solani* damping off with wheat bran culture of *Trichoderma harzianum*" *Phytopathology* 69:64–68 (1979); Papavizas and Lewis, "Physiological and biocontrol characteristics of stable mutants of *Trichoderma viride* resistant to MBC fungicides", *Phytopathology* 73:407–411 (1983); and Paulitz and Baker, "Biological control of Pythium damping-off of cucumbers with *Pythium nunn:* Influence of soil environment and organic amendments" *Phytopathology* 77:341–346 (1987)).

Species of Myrothecium, including *M. roridum,* are known to have strong cellulolytic activity which can be positively correlated with rhizosphere competence and strong competitive saprophytic ability (Ahmad and Baker, "Competitive saprophytic ability and cellulolytic activity of rhizosphere-competent mutants of *Trichoderma harzianum*" *Phytopathology* 77:358–362 (1987b); Domsch et al., "Myrothecium" in Compendium of Soil Fungi, Vol. 1, Domsch et al., eds., Academic Press, London, pp. 481–487 (1980)). Rhizosphere competence is defined as the ability to colonize the region of the root known as the rhizosphere, defined as the zone where maximum populations of soil organisms exist including the root surface, the adjacent soil and the external layer of the root itself (Russell, "Soil Conditions and Plant Growth", Chapter XII, in The Association between Plants and Microorganisms, Longmans, Pub., pp. 224-239 (1961)). *M. roridum* and other species of *Myrothecium* are strong antibiotic producers (Bamburg, "Biological and biochemical actions of trichothecene mycotoxins" *Prog. Mol. Subcell. Biol.* 8:41-110 (1983); Brian et al., "Production of antibiotics by species of *Myrothecium*" *Mycologia* 40:363-368 (1948); Jarvis et al., "Interaction between the antibiotic trichothecenes and the higher plant *Baccharis megapotamica*" *Science* 214:460-462 (1981); and Jarvis et al., "Macrocyclic trichothecene mycotoxins in Brazilian species of *Baccharis*" *Phytopathology* 77:980-984 (1987)). Myrothecium has been demonstrated to reduce root rot caused by *Fusarium* and *Pythium* in peas (Reyes and Dirks, *Phytoprotection* 66:23-29 (1985)).

A few attempts have been made to develop biological methods to control Phytophthora root rot of avocados in the field (Zentmyer, "Biological control of Phytophthora root rot of avocado with alfalfa meal", *Phytopathology*, 53:1383-1387 (1963)). Two avocado groves with soils suppressive to *P. cinnamomi* have been reported (Broadbent and Baker, "Behaviour of *Phytophthora cinnamomi* in soils suppressive and conducive to root rot" *Aust. J. Agric. Res.* 25:121-137 (1974a)). In this case, the continuous incorporation of large quantities of organic material and calcareous amendments partially restored some of the suppressive properties of the native rainforest soil, which naturally supports a microflora and microfauna that inhibits *P. cinnamomi* (Baker, "Biological control of *Phytophthora cinnamomi*", *Proc. Int. Plant Propagators Soc.* 28:72-79 (1978); Broadbent and Baker, supra (1974a); Cook and Baker, "The Nature and Practice of Biological Control of Plant Pathogens", American Phytopathological Society, St. Paul, Minn. 539 pp. (1983); and Rovira, "Organisms and mechanisms involved in some soils suppressive to soilborne plant diseases", in "Suppressive Soils and Plant Disease" Schneider, ed., American Phytopathological Society, St. Paul, Minn. 88 pp. (1982)).

Soils suppressive to Phytophthora have been described from several parts of the world, however, the nature of such suppression is still largely unresolved (Cook and Baker, supra; Scher et al., "Mechanism of biological control in a Fusarium-suppressive soil", *Phytopathology*, 70:412-417 (1980)). Generally, no single physical, chemical, or biological property of a soil has been identified as a primary determinant in soils suppressive to Phytophthora. No single organism has been isolated that could completely reproduce the suppression (Broadbent and Baker, "Association of bacteria with sporangium formation and breakdown of sporangia in *Phytophthora*", *Aust. J. Agric. Res.* 25:139-145 (1974)). Additionally, the suppressive phenomenon was not transferable to new soils (Cook and Baker, supra), as is the case with some soils suppressive to Fusarium (Scher and Baker, supra).

*M. roridum* together with another species (*M. verrucaria*) are well documented as soil microorganisms and have a cosmopolitan distribution (Domsch et al., "Myrothecium", pages 481-487 in: *Compendium of Soil Fungi*, Vol 1, Academic Press (1980); Tulloch, "The Genus Myrothecium Tode ex Fr.," *Mycol. Pap.* 130:1-42 (1972)). They are found in a wide range of soils, especially those high in organic matter, and on a number of other substrates (Boland et al., "Biological control of *Sclerotinia sclerotiorum* with fungi isolated from petals" (Abstr.) *Phytopathology*, 77:115 (1987); Domsch et al., supra; Thode, "*Fusarium solani, Fusarium equiseti* and *Myrothecium verrucaria* as parasites of *Pythium ultimum*", M. S. Thesis, University of California, Davis, (1981); Tulloch, supra).

Pathogens such as *P. cinnamomi*, which attack the roots of their hosts and grow internally until the plant is killed, are difficult to control once penetration of the host root has occurred. Consequently, promising biological control organisms may need to be rhizosphere-competent (Ahmad and Baker, "Rhizosphere competence of *Trichoderma harzianum*, *Phytopathology* 77:182-189 (1987a); Ahmad and Baker, (1987b)) to antagonize the pathogen before infection.

For biological control, an inoculum is used consisting of an aqueous suspension containing the antagonistic organism to be introduced into the soil, or onto a plant surface to fight the pathogen. For applications onto a plant surface, the aqueous suspension may be sprayed or, for applications to certain plant parts such as fruits and tubers, the parts may be dipped in the inoculum. Bran such as wheat bran is an effective and economic food base for introducing specific biological control agents into soils (Hadar et al., "Biological control of *Rhizoctonia solani* damping off with wheat bran culture of *Trichoderma harzianum*", *Phytopathology* 69:64-68 (1979); Lewis and Papavizas, "A new approach to stimulate population proliferation of Trichoderma species and other potential biocontrol fungi introduced into natural soils", *Phytopathology* 74:1240-1244 (1984); Lewis et al., "Effect of mycelial preparations of Trichoderma and Gliocladium on populations of *Rhizoctonia solani* and the incidence of damping-off", *Phytopathology* 75:812-817 (1985); Papavizas and Lewis, "Introduction and augmentation of microbial antagonists for the control of soilborne plant pathogens", pages 305-322 in *Biological Control in Crop Production*. Beltsville Symp. Agric. Res. Vol. 5, Ed. Allanheld, Osmun & Co., Totowa, N.J. (1981)).

It would be useful to provide a means of biological control of plant pathogens such as Phytophthora in soil and on plant surfaces using a microorganism capable of exerting its effect in the presence of other competing microorganisms.

SUMMARY OF THE INVENTION

The present invention meets the need for effective biological control of a plant pathogen such as Phytophthora in soil and on plant surfaces using strains of the fungus Myrothecium.

The invention provides novel strains of *Myrothecium roridum* that are capable of controlling Phytophthora in soil and on plant surfaces.

The invention also provides a method for biological control of Phytophthora in soil and on plants comprising adding to medium containing Phytophthora an inoculum of *Myrothecium roridum* at a rate of from about 10 grams of inoculum/liter of medium to about 50 grams of inoculum/liter of medium to suppress the Phytophthora.. Preferably, the inoculum is added at a rate of 15 grams of inoculum/liter of medium to about 25 grams of inoculum/liter of soil medium. The medium may be soil or water.

The invention includes inocula for biocontrol of Phytophthora in soil and on plant surfaces comprising bran and Myrothecium or a bran/alginate mixture containing Myrothecium. Inoculum containing Myrothecium strain TWm14 may also include a fungicide such as a benzimidazole compound, for example, carbendazim, benomyl or thiabendazole, for reducing the presence of other competing fungi. The Myrothecium is preferably grown on the bran component of the inoculum for from about 5 to about 7 days before use.

BRIEF DESCRIPTION OF THE DRAWINGS

FIG. 1 is a graph of the population density of *P. cinnamomi* after soil amendment with strains of *M. roridum* and Trichoderma sp. as described in Example 1, infra.

FIG. 2 is a graph of the percent inhibition of mycelial growth of *P. cinnamomi* by dilutions of sterile culture filtrates from strains of *M. roridum* as described in Example 1, infra.

FIG. 3 is a graph of the inhibition of zoospore germination of *P. cinnamomi* by dilutions of sterile culture filtrates from strains of *M. roridum* as described in Example 1, infra.

DETAILED DESCRIPTION OF THE INVENTION

In order that the invention herein described may be more fully understood, the following detailed description is set forth.

The present invention relates to novel strains of the fungi Myrothecium and their use in a method of biological control in soil of the plant pathogen Phytophthora. Phytophthora causes root rot in plants such as avocados, tomatoes, tobacco, soybeans, cucumber, green peppers, ornamentals, and citrus. Preferably, for biological control, Myrothecium strains are used in an inoculum of bran, e.g. wheat bran, or bran-alginate introduced into soil or onto plants to suppress growth and colonization of Phytophthora on plants. Alternatively, the Myrothecium is used in an aqueous suspension that may be sprayed onto the surfaces of plants such as roots, stems, leaves and fruit, or into which the plant parts are dipped, to treat Phytophthora infection.

Soils suppressive to *P. cinnamomi* were located in California in eighty year old avocado groves having deep alluvial soils Occurrence of *P. cinnamomi* has been recorded in these groves for 40-50 years, but there has been no significant decline in tree vigor despite the presence of *P. cinnamomi.* The majority of avocado groves with similar alluvial soils and in the same vicinity had declined or had been lost to Phytophthora root rot.

I. ISOLATION OF THE MYROTHECIUM STRAINS a) Soils

Soil samples were obtained from the region of the fine fibrous feeder roots of avocado trees in an avocado grove located in Santa Barbara County, Calif. *Phytophthora ("P.") cinnamomi* has been present in this grove since the early 1940's, however no severe root rot symptoms including loss of foliage, branch dieback and death of the entire tree, nor subsequent tree decline, had been observed. The top 10 cm from which the samples were taken was a sandy loam having the following characteristics: pH 6.8, 3.6% organic matter, 29 μg/g of phosphorus and 512 μg/g of potassium. The presence of *P. cinnamomi* was detected by their characteristic colony morphology, size of their spores and presence of coralloid (coral-like) hyphal swellings (CMI Descriptions of Pathogenic Fungi and Bacteria, No. 113, *Phytophthora cinnamomi,* Waterhouse and Waterston (1966)). Population densities were determined using soil dilution plating and a Phytophthora-selective PARPH agar medium as described by Kellam and Coffey, "Qualitative Comparison of the Resistance to Phytophthora Root Rot in Three Avocado Rootstocks", *Phytopathology* 75:230-234 (1985)). In addition, for certain of the assay procedures used to test for biocontrol of *P. cinnamomi* by Myrothecium strains five artificial mixes or soils were used as follows: UC mix No. 4, pH 5.8, consisting of 50% fine sand, 50% peat moss plus 2.2 kg of dolomite, 1.5 kg of superphosphate, 148 g of $KNO_3$, 148 g of $K_2SO_4$ $m^{-3}$ (Baker, "The U.C. System for Producing Healthy Container-Grown Plants", Univ. of Calif. Division of Agri. Sci., Agricultural Experimental Station, Extension Service, 332 pp. (1957)); a peat-perlite mixture (60:40, v/v), pH 5.8; and three field soils infected with *P. cinnamomi* from Goleta, Camarillo and Santa Paula, Calif., respectively, determined as described above.

The characteristics of the Goleta soil were: a sandy clay loam, pH 7.2, 1.8% organic matter, 29 μg/g of phosphorus, 174 μg/g of potassium, and 921 μg/g of nitrogen. The Camarillo soil was a sandy clay loam having a pH of 6.0, 1.3% organic matter, 21 μg/g of phosphorus, 160 μg/g of potassium and 780 μg/g of nitrogen. The Santa Paula soil was a loam with a pH of 7.4, 10.7% organic matter, 8.8 μg/g of potassium, and 6,675 μg/g of nitrogen.

b) Isolation of Organisms

Isolation of bioassay organisms. Soil was collected from three avocado trees chosen for their exceptional vigor in the grove that exhibited suppressive-soil properties. Four 1-liter samples were collected and combined from the feeder root zone of each tree. One gram of roots was randomly removed from each combined sample, added to 99 ml of sterile distilled water, shaken for 10 min., and a dilution series prepared. One-milliliter samples were plated on King's B medium (King et al., "Two simple media for the demonstration of pycocyanin and fluorescein", *J. Lab. Clin. Med.* 44:301-307 (1954)), and the resultant bacterial colonies transferred to yeast-dextrose agar (1% yeast extract, 2% $CaCO_3$, 2% dextrose, 2% agar). Bacteria were stored either freeze dried, or in 0.85% sterile saline solution at 5° C. Bacteria (110 isolates) from the rhizosphere were screened in randomly chosen groups of three for their ability to suppress Phytophthora root rot. Fungi were isolated by plating 1 ml samples on a modified Martin medium (Papavizas and Davie, "Evaluation of various media and antimicrobial agents for isolation of fungi", *Soil Sci.* 88:112-117, (1959)). They were stored on potato-dextrose agar (PDA) at room temperature or by cryopreservation under liquid nitrogen.

Thirty-six types of fungi isolated from the rhizosphere of avocado roots were included in the final screening greenhouse tests. Strains of the genus Myrothecium and species *Myrothecium roridum* were identified by their morphological characteristics (Tulloch, "The genus Myrothecium Tode ex Fr." *Mycological Papers* 130:1-42 (1972)) including conspicuous, dark-green sporodochia, dark-green conidia (asexual spores borne on specialized hyphae known as conidiophores and produced by Fungi Imperfecti; ascomycetes and a few basidiomycetes) produced on phialides. Conidia are rod-shaped and have dimensions of 5.5 to 7 microns by 1.5 to 2.0 microns.

One strain of *Myrothecium roridum*, obtained as described above, was found to be consistently active in controlling *Phytophthora cinnamomi* in greenhouse tests and was designated strain TW (P4020).

c) Mutagen Treatment

Strain TW of *Myrothecium roridum* was subjected to chemical mutagenesis as described by Davidse, "Resistance to Acylalanine Fungicides in *Phytophthora megasperma* f. sp. *medicaoinis*", *Netherlands Journal of Plant Pathology* 87:11-24 (1981), to obtain mutant strains containing specific selectable markers, (e.g. mutant *M. roridum* strain TWm14 contains a carbendazim marker and strain TWHg14 contains a hygromycin B marker) for evaluation of their biological properties, especially their biological control properties.

Two *Myrothecium roridum* strains obtained by mutagenesis as described above, strain (P4057) TWm14 and strain (P4403) TWHg14 were also found to provide suppression of *P. cinnamomi.*

Cultures of the novel strains of Myrothecium have been deposited in the American Type Culture Collection ("ATCC") and received accession numbers as follows:

| Strain | ATCC Accession No. | Deposit Date |
|---|---|---|
| TW (P4020) | 20963 | October 27, 1989 |
| TWm14 (P4057) | 20964 | October 27, 1989 |
| TWHg14 (P4403) | 20965 | October 27, 1989 |

II. CHARACTERIZATION OF STRAINS OF MYROTHECIUM

Assays To Determine Ability For Biocontrol Using Strains Of Myrothecium

The strains of Myrothecium produced as described above were tested in greenhouse tests to determine the ability to suppress root infection by *Phytophthora cinnamomi* of *Persea indica* seedlings. Greenhouse pot tests were adapted from tests described by Dolan et al., "Protection of Persea species against *Phytophthora cinnamomi* and *P. citricola* by prior inoculation with citrus isolate of *P. parasitica,*" *Phytopathology* 76:194-198 (1986). The tests were performed on seedlings of *P. indica* grown in substrate mixes into which the strains of Myrothecium had been incorporated. After transferring seedlings into the mixtures, the plants were inoculated with a zoospore suspension of *P. cinnamomi.* Several weeks after inoculation, feeder roots were excised and infected root pieces counted to determine percent root infection.

In vitro tests for antibiosis of the fungal isolates were also conducted using cultures of *P. cinnamomi* grown on potato dextrose agar ("PDA") in the presence of strains of Myrothecium. In addition, the cellulolytic abilities of *M. roridum* were evaluated using a mutant strain of *M. roridum* grown in a basic salts medium and cellulose. The effect of culture filtrates of *M. roridum* on mycelial growth and sporulation and zoospore germination of *P. cinnamomi* were also studied using the methods of Coffey and Joseph, "Effects of Phosphorous Acid and Fosetyl-Al on the Life Cycle of *Phytophthora cinnamomi* and *P. citricola,*" *Phytopathology* 75:1042-1046 (1985).

III. USE OF MYROTHECIUM IN THE BIOLOGICAL CONTROL OF PHYTOPHTHORA CINNAMOMI

In general, the procedure for testing strains of Myrothecium for biological control consists of adding an effective amount of the inoculum of the Myrothecium furnished in an appropriate medium to soil which contains the pathogen *Phytophthora cinnamomi.* The inoculum is mixed into the infected soil and inhibits the activity of the *Phytophthora cinnamomi* organisms present in the soil. The progress of the treatment may be monitored by determining the population density of *P. cinnamomi* in the soil before, during and after treatment with Myrothecium, for example by suspending soil containing *P. cinnamomi* in 0.1% agar, then placing the suspension on cornmeal-PARPH agar (PARPH, pimaricin, ampicillin, rifampicin, pentachloronitrobenzene, hymexazol is an antibiotic medium which is selective for Phytophthora spp. and is described in Kellam and Coffey, (1985) supra) and observing for colonies of *P. cinnamomi* as described above.

The amount of inoculum containing Myrothecium effective in treatment of plants infected with *P. cinnamomi* may be determined experimentally by measuring the presence or absence of *P. cinnamomi* in root pieces (Kellam and Coffey, supra) and the appropriate level of Myrothecium retained in the soil by periodically sampling the soil to calculate the population density of Myrothecium present over time in a manner similar to that for determining *P. cinnamomi* using agar as described above. In addition, rhizosphere population density, defined as the population density in the interfacial volume between the plant roots and the bulk of the soil in which the largest concentration of soil microorganism live, may be determined for strain TWm14 by placing a suspension obtained from washing roots of the plant on carbendazim-selective PDA medium. Similarly, the rhizosphere population density for strain TWHg14 may be determined on hygromycin-selective PDA medium.

In general, an inoculum rate of about 10 grams of inoculum/liter of medium to about 50 grams of inoculum/liter of medium, for example soil or water, and preferably about 15 grams of inoculum/liter of medium to about 25 grams of inoculum/liter of medium will be effective to reduce infection by *P. cinnamomi* in the presence of a population density of from about 1 to 50 colony forming units (cfu), i.e. propagules and spores of *P. cinnamomi,* per gram dry weight of soil.

In general, the inoculum may consist of any suitable material including natural soils and artificial soils such as peat-perlite containing 60:40 v/v peat and perlite, pH 5.8; or mixtures containing sand, peat moss, dolomite and other compounds, for example University of California ("UC") mix No. 4, pH 5.8, consisting of 50% fine sand, 50% peat moss plus 2.2 kg of dolomite, 1.5 kg of superphosphate, 148 g of $KNO_3$, 148 g of $K_2SO_4\,m^{-3}$ as described by Baker, "The U.C. system for Producing Healthy Container-Grown Plants", University of California Service, 332 pp. (1957). The Myrothecium may be pre-grown on bran, for example, wheat bran, and the colonized bran mixed with the remaining inoculum material. The inoculum may also include a fungicide such as a benzimidazole compound for example carbendazim, benomyl or thiabendazole for use with *Myrothecium roridum* strain TWm14.

A preferred inoculum consists of bran-alginate pellets containing the Myrothecium. Briefly, the fungus is grown on bran, such as wheat bran, and the conidia grown on PDA and then removed and re-added to the bran for colonization. When the fungus colonizes the bran it is homogenized and sodium alginate added. The bran-alginate mixture is passed into a $CaCl_2$ solution to form spherical calcium alginate pellets which are then dried and stored. This inoculum has the advantage of permitting longer storage periods of at least 12 months at 24° C. (Bran alone has to be used within 1 to 2 weeks). The amount of Myrothecium i.e., colony forming units or cfu per gram of medium, for example, soil, may be calculated to determine ranges of amounts of Myrothecium useful for biocontrol of given populations of Phytophthora.

The result of adding Myrothecium to soil in which plants infected by *P. cinnamomi* are growing is the decrease, or elimination, of root infection that can lead to root rot in plants.

In order that the invention described herein may be more fully understood, the following examples are set forth. It should be understood that the examples are for illustrative purposes only and are not to be construed as limiting the scope of this invention in any manner.

EXAMPLE 1

This example describes the evaluation of Myrothecium as a biological control agent for suppression of *Phytophthora cinnamomi* on *Persea indica* plants, a relative of the avocado tree, using screening bioassays to characterize fungal isolates for suppressive ability and greenhouse tests of artificial soil mixtures and natural soils infested with the pathogen.

All greenhouse experiments were performed at least twice, with 12-15 replications using completely randomized block designs. Data were statistically analyzed by one-way ANOVA. Duncan's multiple range tests or a Least Significant Differences (LSD) test were used to separate means. When applicable, multiple regression analysis was performed. Results were analyzed with a MSTAT computer program (Michigan State University, Version 4.0 (1985)). Percent values were subjected to arcsin transformation before analysis.

Plants. Six week old seedlings of *P. indica* previously grown in sand were used for screening fungi. All plants were grown in the greenhouse with natural light and at a temperature in the range of between 18° C. and 29° C.

Preparation of inoculum of *P. cinnamomi*. For zoospore inoculum, the fungus was grown on cleared V8C agar (10% V-8 juice, 1% $CaCO_3$, clarified by centrifugation, 2% agar) for 3-4 days. Ten 5 mm diameter agar/mycelium disks were placed in a 9 cm diameter plastic petri dish and flooded with a V8C broth diluted 1:4. *P. cinnamomi* was incubated for 24 hr at 24° C. After removing the broth and washing the mycelium mats three times with distilled water, 10 ml of a 1% non-sterile soil extract, previously filtered through Whatman No. 1 paper, was added to the plates. The fungus was incubated in the dark for 5-6 days at 24° C. for sporangial formation. Next, the soil extract was replaced with fresh extract and the fungus chilled at 5° C. for 1 hr to release zoospores. Zoospores were counted with the aid of a hemacytometer and diluted with non-sterile soil extract to the desired concentration.

An alternative inoculation method involved millet seeds (300 g), which were autoclaved for 1 hr and inoculated with blended mycelium from the two 5-day-old PDA (Difco Laboratories, Detroit, Mich.) colonies of the fungus suspended in 200 ml of sterile distilled water. After 10 days of incubation at 24° C., the millet inoculum was blended twice (1 min. at high speed) in a blender and mixed into UC mix No. 4 (2% v/v). The soil mixture was maintained at approximately 12% soil moisture at approximately 24° C. After 5-7 days, the population density of *P. cinnamomi* in the mix was determined by the dilution-plate technique on cornmeal-PARPH, medium selective for Phytophthora (Kellam and Coffey, (1985) supra). This medium consisted of 1.8% Difco cornmeal agar (Difco laboratories, Detroit, Mich.) with (per milliliter) 133 $\mu$g of pentachloronitrobenzene, 125 $\mu$g of ampicillin, 10 $\mu$g of rifampicin, 10 $\mu$g of pimaricin, and 50 $\mu$g of hymexazol. The infested potting mix then was diluted with non-infested mix to give about 15-30 colony forming units (cfu) of *P. cinnamomi* per gram of dry mix.

In addition, three naturally infested field soils conducive to Phytophthora from three avocado groves with severe root rot in southern California (Goleta, Camarillo and Santa Paula) were collected from underneath diseased avocado trees, sifted through a 10 mm mesh sieve, and used directly as an inoculum source.

GREENHOUSE EXPERIMENTS

Bioassay with Myrothecium

Seedlings of *P. indica*, grown in sand for 6 weeks were transferred to 5 cm diameter plastic pots containing UC mix No. 4 or peat-perlite mixture, into which the potential fungal antagonists had been incorporated. Fungi were grown on wheat bran for 5-7 days at 24° C. in the dark. Fifty milliliters (ml) of fungal spore suspension ($1 \times 10^6$ spores/ml), or twenty 3 mm diameter, agar mycelium disks removed with a sterile cork borer from the margins of actively growing colonies, were added to 500 ml Erlenmeyer flasks containing 50 g of autoclaved (1 hr) bran and incubated at 24° C. After 5-7 days, the colonized bran was mixed either with UC mix No. 4 or peat-perlite mixture at different ratios (w/v) ranging from 1 to 50 g/L. Controls consisted of UC mix No. 4 or the planting mixes plus uninoculated wheat bran.

Potassium phosphonate, a fungicide control, was prepared by mixing equimolar amounts of phosphorous acid and potassium hydroxide and titrating with the latter to a final pH of 6.8. Five or 10 ml of a 500 $\mu$g/ml solution of potassium phosphonate were applied as a soil drench to each plant 1 wk before inoculation. Trichoderma spp. (isolates 72 (P4163), 86 (P4173), 104 (P4187), isolated from same soil as strain TW from Santa Barbara County) and a strain of *T. hamatum* ((P4162) isolated from a soil in Fallbrook, Calif.) grown on wheat bran, which possessed no strong antagonistic effects against *P. cinnamomi*, also were used as additional controls in different experiments. Two weeks after transferring seedlings of *P. indica* into the soil/bran mixtures, plants were inoculated with 5 ml of a zoospore suspension of *P. cinnamomi* ($1 \times 10^4$ spores/ml unless stated otherwise), which was placed 2-3 cm from opposite sides of the stem base at a depth of 3-4 cm.

Four to six weeks after inoculation with *P. cinnamomi*, experiments were terminated and the root system washed free of soil. Feeder roots were cut into 1 cm sections and 20 randomly selected pieces were plated on cornmeal-PARPH agar. After 36-48 hr at 24° C., infected root pieces were counted and results expressed as percent root infection.

Population density of *P. cinnamomi* in artificially and naturally infected soil. Soil samples were collected from three to five randomly chosen plants per treatment. Artificially infested soil samples (10 g) and naturally infested soil samples (50 g) were suspended in 100 ml of 0.1% agar in Styrofoam cups and mixed on a rotary shaker at 200 rpm for 30 min. One ml of the soil-agar slurry was placed on each of five plates of cornmeal-PARPH agar. After 48 hr, the soil was washed off the plates and colonies of *P. cinnamomi*, recognizable by their distinctive growth with clusters of hyphal swellings, were counted. Population densities were expressed as colony-forming units per gram of soil (cfu/g), and were used to determine suppressive effects of fungal isolates on Phytophthora.

Figure 1:
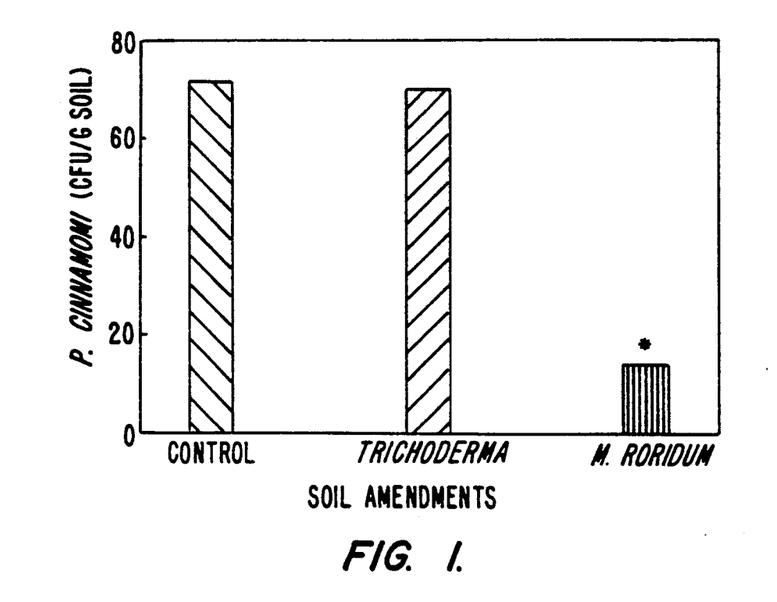
Figure 2:
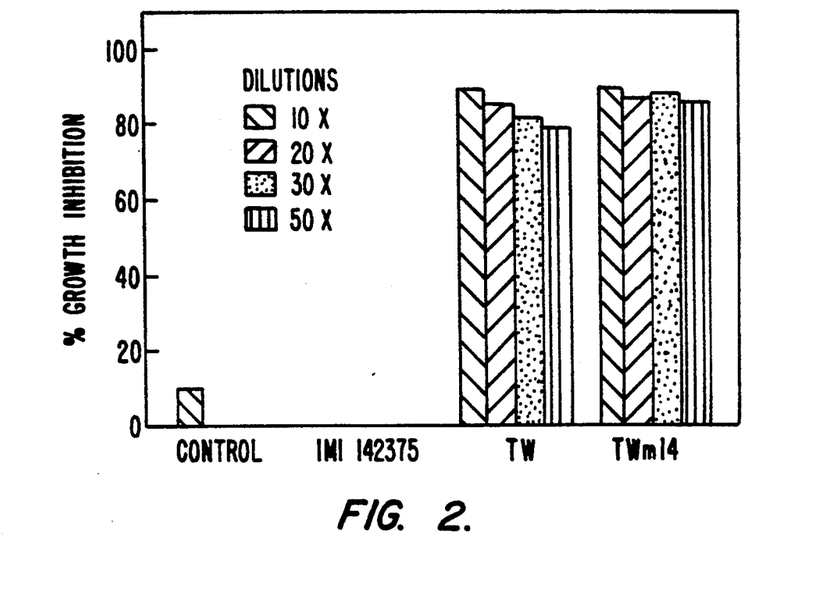
Figure 3:
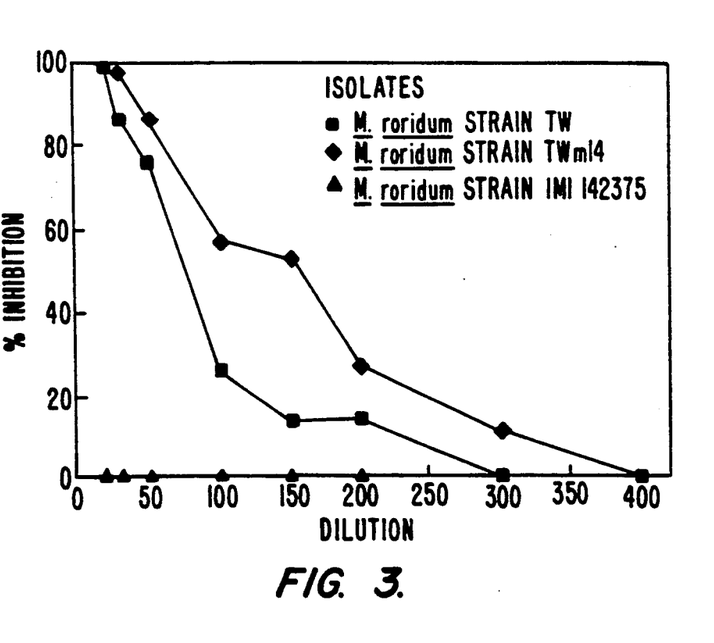

In the UC mix, an artificially high inoculum level of 15–30 cfu/g of soil of *P. cinnamomi* was used, whereas 3–6 cfu/g were present in three naturally infested field soils. In the UC mix and field soils, soil amendment with strains TW and TWm14 of *M. roridum* significantly suppressed root rot of *P. indica*, compared with a non-amended control (Table 1). A Trichoderma sp., isolate 104, isolated from the same avocado soil as the strain of *M. roridum*, had no consistently suppressive effect. Soil samples were analyzed for *P. cinnamomi* at the conclusion of the experiments. Population density of the pathogen was significantly lower in treatments with *M. roridum* (FIG. 1).

TABLE 1

Effect of wild-type strain TW and carbendazim-resistant strain TWm14 of *Myrothecium roridum*, grown on wheat bran, on percent root infection of seedlings of *Persea indica* and on the population density of *Phytophthora cinnamomi* in artificially infested UC mix No. 4 and three naturally infested field soils.

| Treatments[x] | Percent Root Infection | | | | Soil Population Densities of *P. Cinnamomi* (cfu/g[y]) |
| | U.C. Mix No. 4 | Field Soils | | | |
| | | Goleta | Camarillo | St. Paula | |
| --- | --- | --- | --- | --- | --- |
| Control | 81.3 a[z] | 92.5 a | 57.5 a | 70.5 a | 46 |
| Trichoderma sp. (isolate 104) | 81.7 a | 94.0 a | 66.5 a | 61.0 ab | 32 |
| Myrothecium roridum (TW) | 40.5 b | 54.0 b | 11.5 b | 30.5 b | na |
| M. roridum (TWm14) | 48.7 b | 32.5 b | 38.0 ab | 27.0 b | 12 |

[x]All plants were grown in UC mix No. 4 amended with wheat bran inoculum (2.5%, w/v) for 2 wk before transplanting into field soils naturally infested with *P. cinnamomi* (Goleta and Camarillo, sandy clay loams; Santa Paula, loam). No wheat bran was used in the control treatment.
[y]Colony forming units (cfu/g soil of *P. cinnamomi* for UC mix No. 4 after 4 weeks of incubation; na = not assessed.
[z]Means within columns followed by the same letter are not significantly different according to Duncan's multiple range test (P = 0.05).

Production of Mutant Strains of *M. roridum*.

Chemical mutagenesis was performed to obtain mutant strains of Myrothecium for evaluating their biligical control properties and for use in soil population studies using a selective medium containing the appropriate compound (e.g. carbendazim) highly inhibitory to the wild type strain (strain TW). The method used was that described by Davidse, supra. Carbendazim-resistant strains were prepared as follows. Conidial suspensions (approximately $1 \times 10^7$ conidia/ml) were incubated in an aqueous solution of the chemical mutagen N-methyl-N'-nitro-N-nitrosoguanidine (75 µg/ml) for 20 min. After centrifuging at high speed for 2 min, sedimented conidia were washed three times with sterile distilled water. One-ml samples of the conidial suspension were placed on petri dishes and overlaid with a selective PDA medium containing (per ml) 100 µg of carbendazim, plus 125 µg of ampicillin, 10 µg of rifampicin, and 125 µg of chloramphenicol. Fifty-eight fungicide-resistant mutants were recovered and, after repeated subculture, were determined to be phenotypically stable with respect to level of fungicide resistance, colony morphology, and antibiosis in vitro against *P. cinnamomi*. One of these mutants, strain TWm14, was selected for use in further experiments because of its fast growth and prolific conidial production on a carbendazim-selective PDA medium. Strain TWm14 has been deposited with the ATCC and has received accession number 20964. This mutant can be used to provide integrated biocontrol by decreasing competition from other organisms through application to the soil or other substrate or on plant surfaces, of any benzimidadazole fungicide, including carbendazim, benomyl and thiabendazole.

Carbendazim-resistant mutants of *M. roridum* were tested on PDA for changes in growth rate, colony morphology, and in vitro antibiosis of *P. cinnamomi* as compared to strain TW of *M. roridum*. No differences in these characteristics could be detected among 58 mutants studied. Three randomly selected mutants (TWm14, TWm15, and TWm30) were tested further for their biological control capabilities in comparison with the wild type. The standard bioassay method with 2.5% bran-peat perlite mixture (w/v) and inoculation with zoospores was used as described above. No significant differences were found among these three resistant mutants and the wild-type TW in controlling *P. cinnamomi* in the artificially infested UC mix.

In addition, mutant strains of *Myrothecium roridum* resistant to the antibiotic hygromycin were prepared as described above except 5 µg/ml of hygromycin B (Calbiochem, San Diego, Calif.) was added in place of the carbendazim. (Ampicillin, rifampicin and chloramphenicol were not used). Fourteen mutants were recovered and a mutant strain TWHg14 (p4403) was selected for further testing because of its fast growth and prolific conidial production. Strain TWHg14 has been deposited with the ATCC, and has received accession number 20965.

Hygromycin-resistant mutant strain TWHg14 (p4403), ATCC No. 20965 was observed to perform equivalent to strain TW and strain TWm14 in experiments to determine the effects of the strain on *P. cinnamomi* infection of *Persea indica* seedlings. In an experiment identical to those described for strain TW (Tables 3 and 4), strain TWHg14 (p4403) performed the same as strain TWm14 (P4057). Strain TWHg14 was prepared in both a wheat bran and bran-alginate inoculum at 20 g per liter volume of soil. Both formulations of strain TWHg14 suppressed *P. cinnamomi* root rot on *Persea indica* seedlings. Table 2 summarizes these results.

TABLE 2

Effect of different strains of *Myrothecium roridum* grown on wheat bran or bran-alginate on percent root infection of seedling of *Persea indica* 4 weeks after inoculation with millet-grown inoculum of *Phytophthora cinnamomi* (cfu/g soil)

| Treatments | Percent Root Infection |
| --- | --- |
| Control | 85.3 a[z] |

TABLE 2-continued

Effect of different strains of *Myrothecium roridum* grown on wheat bran or bran-alginate on percent root infection of seedling of *Persea indica* 4 weeks after inoculation with millet-grown inoculum of *Phytophthora cinnamomi* (cfu/g soil)

| Treatments | Percent Root Infection |
| --- | --- |
| TWm14 (P4057) (10 g bran) | 77.3 ab |
| TWHg14 (P4403) (10 g bran) | 69.0 abc |
| TWm14 (P4057) (20 g bran) | 63.3 bc |
| TWHg14 (P4403) (20 g bran) | 50.0 c |

[z]Values within columns followed by the same letter (a, b, c) are not significantly different according to Duncan's multiple range test (P = 0.05).

Population density of *M. roridum* in soil. Ten gram soil samples containing *M. roridum*, strain TWm14, were suspended in 100 ml of $H_2O$ in styrofoam cups and placed on a rotary shaker at 200 rpm for 30 min. Rhizosphere population density was determined by vigorously washing whole roots of *P. indicia* in 20 ml $H_2O$. One ml samples of these suspensions (three replicates) were used for dilution series on carbendazim-selective PDA medium. After 4-5 days, colonies of *M. roridum* were counted. Population densities were expressed as colony-forming units per gram (cfu/g) of soil.

Two weeks after bran was mixed with potting mix, samples from the root ball had a high population density (greater than ($>1 \times 10^8$ cfu/g) of carbendazim-resistant mutant TWm14. A second assay of TWm14 after 6 weeks showed that the initial population density had dropped, but still was $>1 \times 10^5$ cfu/g in the rhizosphere. The overall percent root infection of *P. indica* caused by *P. cinnamomi* in the TWm14 treatment was 49% compared with 81% for the control (Table 1). In addition, the population density of *P. cinnamomi* dropped from initially 33 to 12 cfu/g in the same treatment. There was no decrease in pathogen population in the controls (Table 1). TWm14 also was recoverable after 6 weeks from most root pieces plated on carbendazim-selective medium.

Evaluation of microorganisms. Because zoospores of *P. cinnamomi* are considered one of the primary infectious agents, different levels of zoospore inoculum were tested. Zoospore inoculum directly applied in the vicinity of the root ball of *P. indica* built up a high population density of *P. cinnamomi*, able to kill most of the control plants during the first week after inoculation.

The three strains of Myrothecium (strain TW, TWm14 and TWHg14) initially isolated as described above were tested repeatedly with different inoculum levels, methods, and soil regimes to determine the consistency of initial results. Strain TW of *M. roridum* consistently and significantly (P=0.05) suppressed root infection at three inoculum levels of *P. cinnamomi* (Table 3). Besides UC mix No. 4, a peat-perlite mixture, routinely used in nurseries as a rooting medium for woody cuttings such as avocado, was tested as a medium for incorporation of bran-grown *M. roridum*. Again, seedlings of *P. indica* inoculated with zoospores of *P. cinnamomi* exhibited very little disease in all experiments, even where high levels of inoculum ($5\times10^4$ zoospores/ml, 10 ml/plant) were used.

TABLE 3

Effect of different fungal isolates grown on wheat bran on the percentage of root infection of *Persea indica* inoculated with different zoospore concentrations of *Phytophthora cinnamomi*

| Treatments[x] | Percent root infection Zoospore/ml $1\times10^{3}$[y] | $0.7\times10^4$ | $4\times10^4$ |
| --- | --- | --- | --- |
| Control | 73 ab[z] | 78 a | 91 a |
| Trichoderma sp. (isolate 86) | 47 b | 86 a | 61 b |
| Trichoderma sp. (isolate 72) | 78 a | 67 a | 43 b |
| *Trichoderma hamatum* | | 89 a | 67 ab |
| *Myrothecium roridum* (strain TW) | 16 c | 5 b | 46 b |
| Potassium phosphonate | 9 c | | 16 b |

[x]Fungi grown on wheat bran for 5 days at 24° C. and added to UC mix No. 4 at 2.5% bran (w/v). No bran was used in the control; potassium phosphonate was used at the rate of 500 μg/ml (pH 6.2, 5 ml/pot.
[y]Zoospore suspensions of *P. cinnamomi* applied at 5 ml/plant.
[z]Means within columns followed by the same letter (a, b, c) are not significantly different according to Duncan's multiple range test (P = 0.05).

In addition, reproducible results were obtained in tests for control of *P. cinnamomi* on *Persea indica* using the following additional species and strains of Myrothecium:

*M. masonii* (strain P4023, ATCC No. 24426);

*M. leucotrichum* (strain P4078, CBS (Centraalbureau voor Schimmelcultures, Baarn, Netherlands) No. 278.78); and *M. verrucaria* (strain P4019, ATCC No. 36872).]

Effect of incorporation different forms of the antagonist *M. roridum*, strain TW, into soil. Wheat bran containing *M. roridum* strain TW significantly suppressed root rot in *P. indica*. Liquid culture filtrates, conidial suspensions, or blended mycelium of *M. roridum* did not suppress *P. cinnamomi*.

Effect of bran inoculum concentration. *M. roridum* (strain TW) was effective in the range of 15 grams/liter to 25 grams/liter (w/v) bran inoculum added to UC mix No. 4 (Table 4). Below 10 grams/liter (w/v) the results were inconsistent. A temporary retardation of the growth of transplanted seedlings of *P. indica* sometimes was noted with 35 grams to 50 grams of bran inoculum of *M. roridum*. This undesirable effect was overcome by a slight change in transplanting technique, which involved placing the root ball of *P. indica* on a 2 to 5 mm thick layer of UC mix No. 4 placed on top of the bran/soil mixture. Two Trichoderma spp. tested as controls did not significantly inhibit disease development. Therefore, a range of from about 10 grams/liter to about 50 grams/liter (w/v) of bran or bran-alginate and preferably about 10 grams/liter to about 25 grams/liter containing *M. roridum* strains TW, TWm14 and TWHg14 grown for from about 5 to about 7 days on the bran, provides a suitable inoculum for use in suppression of Phytophthora.

TABLE 4

Effect of different fungal isolates grown on wheat bran and added at three rates in UC mix No. 4 on the percent root infection of seedlings of *Persea indica* 4 weeks after inoculation with a zoospore suspension of *Phytophthora cinnamomi*

| Treatments[x] | Percent root infection g of bran/fungus mixture per liter UC mix No. 4 25 (2.5%, w/v) | 15 (1.5%, w/v) | 5 (0.5%, w/v)4 |
| --- | --- | --- | --- |
| Control | 77.9 a[z] | 72.9 ab | 47.7 b |

TABLE 4-continued

Effect of different fungal isolates grown on wheat bran and added at three rates in UC mix No. 4 on the percent root infection of seedlings of *Persea indica* 4 weeks after inoculation with a zoospore suspension of *Phytophthora cinnamomi*

| | Percent root infection g of bran/fungus mixture per liter UC mix No. 4 | | |
|---|---|---|---|
| Treatments[x] | 25 (2.5%, w/v) | 15 (1.5%, w/v) | 5 (0.5%, w/v)[4] |
| Trichoderma sp. (isolate 86) | 67.4 a | 77.5 a | 52.1 ab |
| Trichoderma sp. (isolate 72) | 86.0 a | 46.7 b | 80.8 a |
| *Myrothecium roridum* (strain TW) | 4.7 b | 15.7 c | 67.6 ab |
| Potassium phosphonate | | 12.1 c | 9.4 c |

[x]Fungi grown on wheat bran for 5 days at 24° C. and added to UC mix No. 4. No bran was used in the control; potassium phosphonate was used at the rate of 500 μg/ml (pH 6.2, 10 ml/pot). All treatments were inoculated with zoospore suspension of *P. cinnamomi* (5 ml, 1 × 10⁴ zoospores/ml).
[z]Means within columns followed by the same letter (a, b, c) are not significantly different according to Duncan's multiple range test (P = 0.05).

EXAMPLE 2

This example describes characterization of the antibiosis properties of the 52 fungal isolates of 12 species of Myrothecium including, in addition to *M. roridum*, *M. atroviride* (CBS 244.78), *M. masonii* (ATCC 24426) and *M. verrucaria* (ATCC 36872) in vitro (Table 5).

In vitro experiments were repeated twice with three replications. Analysis of data was performed as described above in Example 1.

In vitro experiments. Fifty-two isolates of 12 species of Myrothecium from a variety of sources, including international culture collections, were tested in vitro for antibiosis against *P. cinnamomi* and *Penicillium digitatum* (Table 5). Cultures of *P. cinnamomi* were grown on PDA in the presence of potential fungal antagonists. Agar disks (3 mm diameter) from the margin of 5 day old fungal colonies (Myrothecium) were placed 30 mm from 5-day-old colonies of *P. cinnamomi* and effects on its growth monitored daily with a final reading after 5 days.

As shown in Table 5, several species of Myrothecium were observed to inhibit the growth of *P. cinnamomi* in vitro. Isolates of *M. roridum, M. leucotrichum, M. atroviride.* and *M. verrucaria* were highly active in their antibiosis effects on both *P. cinnamomi* and *Penicillium digitatum*. Growth of *P. cinnamomi* was almost totally inhibited by *Myrothecium roridum* strain TW, the hyphae forming thick clusters of hyphal swellings. However, *M. roridum* was a slow grower compared with *P. cinnamomi* and needed a longer period of time to establish on PDA. These results demonstrate that antibiosis properties of Myrothecium, including strain TW of *Myrothecium roridum*, are strong. Antibiosis is an important component of biological control, indicating that Myrothecium should be useful in biological control of *Phytophthora cinnamomi*.

TABLE 5

Antagonistic Effect of Strains of Myrothecium species Against *Phytophthora cinnamomi* and *Penicillium digitatum* in vitro

| Species of Myrothecium, | Strains Tested | Inhibitory *P. cinnamomi* | Against *P. digitatum* |
|---|---|---|---|
| *M. cinctum* | 12 | 0 | 0 |
| *M. leucotrichum*[a] | 6 | 2 A | 5 A |

TABLE 5-continued

Antagonistic Effect of Strains of Myrothecium species Against *Phytophthora cinnamomi* and *Penicillium digitatum* in vitro

| Species of Myrothecium, | Strains Tested | Inhibitory *P. cinnamomi* | Against *P. digitatum* |
|---|---|---|---|
| *M. inundatum* | 5 | 4 B | 1 B |
| *M. carmichaelii* | 1 | 0 | 0 |
| *M. atroviride*[b] | 1 | 1 A | 1 B |
| *M. masonii* | 1 | 0 | 0 |
| *M. prestonii* | 2 | 0 | 0 |
| *M. graminis* | 2 | 0 | 0 |
| *M. tongaense* | 1 | 0 | 0 |
| *M. bisetosum* | 1 | 0 | 0 |
| *M. verrucaria*[c] | 7 | 6 A | 4 A |
| | | 1 B | 3 B |
| *M. roridum*[d] | 13 | 12 A | 7 A |
| | | 1 C | 5 B |
| | | | 1 C |

[a]Isolates P4022, P4034, P4073, P4076, P4077 and P4078 were active.

[b]Isolate P4030 was active.

[c]Isolates P4019, P4074, P4075, P4085, P4087, P4088, P4089 were active.

[d]Isolates P4015, P4016, P4020 (strain TW), P4025, P4026, P4027, P4036, P4041, P4042, P4043, P4048, P4049 were active.

A = complete inhibition

B = intermediate inhibition

C = no inhibition

In tests with *Persea indica* seedlings, isolates of *M. roridum, M. verrucaria* and *M. leucotrichum* were highly effective in controlling Phytophthora root rot.

Strain TW (P4020) of *M. roridum* was screened in vitro against different Phytophthora species (Table 6) plus a wider range of different fungal pathogens (Table 7) using the procedures described in Example 2. Activity was obtained against the majority of Phytophthora species (Table 6) including *P. cinnamomi, P. drechsleri, P. parasitica* (*P. nicotianae*), *P. palmivora* and *P. megasperma* f.sp. *glycinea*. Activity against *Rhizoctonia solani*, Verticillium, Penicillium, Botrvtis and Alternaria was also present. As Table 7 shows, *Myrothecium roridum* strain TW was also effective against a wide range of plant pathogenic fungi.

TABLE 6

Antagonistic effect of a *Myrothecium roridum* strain TW (P4020) on some Phytophthora species in vitro

| Species | Host | Inhibitory effect |
|---|---|---|
| *P. capsici* MF4 | Black pepper | 2 |
| *P. capsici* | Green pepper | 2-3 |
| *P. citrophthora* | Citrus | 2-3 |
| *P. citrophthora* | Cacao | 2-3 |
| *P. megasperma* f. sp. *medicaginis* | Alfalfa | 2-3 |
| *P. parasitica* | Citrus | 2-3 |
| *P. megasperma* | Douglas Fir | 3 |
| *P. megasperma* f. sp. *glycinea* | Soybean | 4 |
| *P. palmivora* | Cacao, coconut | 4 |
| *P. parasitica* (*P. nicotianae*) | Tobacco | 4 |
| *P. syringae* | Almond | 4 |
| *P. cinnamomi* | Avocado | 4 |
| *P. drechsleri* | Cucumber, melons | 4 |

Rating: 1 = No inhibitory effect to 4 = Strong growth inhibition

TABLE 7

Antagonistic effect of a *Myrothecium roridum* strain TW (P4020) on some plant pathogenic fungi in vitro

| Pathogen | Inhibitory effect |
|---|---|
| *Armillaria mellea* | 1 |
| *Fusarium solani* | 1 |
| *Cladosporium herbarum* | 1 |
| *Fusarium oxysporum* | 1-2 |
| *Pythium ultimum* | 1-2 |

TABLE 7-continued

Antagonistic effect of a *Myrothecium roridum* strain TW
(P4020) on some plant pathogenic fungi in vitro

| Pathogen | Inhibitory effect |
|---|---|
| *Rhizoctonia solani* | 2 |
| *Verticillium albo-atrum* | 2 |
| *Penicillium italicum* | 2 |
| *Alternaria alternata* | 2 |
| *Botrytis cinerea* | 2–3 |
| *Colletotrichum graminicolum* | 2–3 |
| *Rhizopus stolonifer* | 2–3 |
| *Verticillium dahliae* | 3 |
| *Monilinia fructicola* | 3 |
| *Geotrichum candidum* | 3 |
| *Penicillium digitatum* | 4 |

Rating: 1 = No inhibitory effect to 4 = Strong growth inhibition

Cellulolytic activity of *M. roridum*. To test qualitatively the cellulolytic abilities of *M. roridum* as an indication of the potential rhizosphere competence of *M. roridum*, the wild type (TW) and mutant strain (TWm14) of *M. roridum* were grown in a basic salts medium at pH 7.0 containing (g/L): $KH_2PO_4$, 1.0; $K_2HPO_4$, 1.0; $NH_4NO_3$, 1.0; $CaCl_2$, 0.02; $MgSO_4$ 7 $H_2O$, 0.2; $FeCl_3$ (saturated solution), 2 droplets; cellulose (Sigmacell Type 100, Sigma, St. Louis, Mo.), 4.0. Spore suspensions ($1\times10^6$ spores/ml) from 7 day old cultures grown on PDA were transferred to 100 ml of salts medium in 250-ml Erlenmeyer flasks. Controls consisted of medium without fungus, a medium without cellulose but with the fungus, and Trichoderma sp., isolate 104, grown on the cellulose medium. Cultures were incubated at room temperature for 4 weeks and visually checked periodically for fungal growth and cellulose residue. Results indicated that both *M. roridum* strain TW and strain TWm14 were highly effective in completely degrading cellulose and grew well on this product. This demonstrates the potential rhizosphere competence of these strains and also their ability to colonize a wide range of cellulose-based products that could be used as delivery systems for these biocontrol agents in soils.

Both wild-type and mutant strains of *M. roridum* grew readily in the presence of cellulose powder as the only carbon source. After 4 weeks of incubation, *M. roridum* formed a dense layer of mycelium and no free cellulose was left in the flask, whereas the Trichoderma sp. used as a control formed a less dense mycelium, and free cellulose remained in the bottom of the flasks. No growth occurred in the control without cellulose.

Effect of culture filtrates on growth and sporulation of *P. cinnamomi. M. roridum* strains TW and TWm14 were grown for 5–7 days at 24° C. in a basic salts medium (pH 6.4) composed of (g/L): $K_2HPO_4$, 0.2; $NH_4NO_3$, 0.3; $CaSO_4$, 0.2; $MgSO_4$ $7H_2O$, 0.2; sucrose, 2; yeast extract, 4; Difco casamino acids, 2. A conidial suspension from a 7 day old culture of *M. roridum* strains Tw and TWm14 was transferred to 100 ml of medium in 250 ml Erlenmeyer flasks to give a final spore concentration of $1\times10^4$/ml. Flasks were shaken on a rotary shaker at 130 rpm for 5 days. Broth was separated from mycelium by filtration through Whatman No. 1 paper, then filter-sterilized with a 0.2-μm Nalgene filter (Nalgene, Rochester, N.Y.). Dilution series of the sterilized growth medium were prepared to test the antifungal activity of the filtrate against *P. cinnamomi;* salts medium or $H_2O$ were added to control plates. One milliliter of each dilution was placed in a petri plate and amended with 9 ml of molten PDA. When solidified, agar disks with *P. cinnamomi* were placed in the center of each petri plate. Plates were incubated at 24° C. and the growth monitored daily.

The effect of the culture filtrates on zoospore germination also was tested. Three sterile cellophane squares (10 $mm^2$) were placed on the surface of PDA in 9 cm diameter plastic petri dishes, 5–10 μl of a zoospore suspension ($5\times10^5$/ml) of *P. cinnamomi* was spotted in the center of each square, and the droplet was allowed to dry completely before incubating at 24° C. for 10–13 hr. Liquid growth medium of another strain of *M. roridum* (IMI 142375) was used for comparison. The cellophane squares were removed from the agar and placed on a micro-slide, and droplets of 2% lactophenol-cotton blue were used to stop fungal growth. Percentage of germinated spores was determined by counting 100 spores on each of three cellophane squares.

All dilutions of sterile culture filtrates from two strains of *M. roridum* grown on a basic salts medium for 6 days, when added to PDA, strongly inhibited mycelial growth of *P. cinnamomi* (FIG. 2). A 10-fold dilution of the liquid growth medium inhibited the growth of the fungus for at least 60 hr; subsequent growth was very slow and the mycelium was distorted. In the control, *P. cinnamomi* reached the edge of plates after 72 hr. A fourfold dilution caused complete inhibition of the pathogen over a period of 8 days. The pathogen, however, resumed normal growth when transferred to nonamended PDA.

A 20-fold dilution of growth medium of TW and TWm14 completely inhibited zoospore germination of *P. cinnamomi,* and a 100-fold dilution prevented germination of cysts by 26 and 59%, respectively (FIG. 3). There was, however, no significant difference between the wild-type and the mutant strain in their activity. In comparison, all dilutions of growth medium of IMI 142375 (CAB Mycological Institute, UK) had no activity against zoospores of *P. cinnamomi* (FIG. 3).

The present invention demonstrates the ability of a strain of *M. roridum,* isolated from soil suppressive to Phytophthora in southern California, to suppress *P. cinnamomi* in tests with susceptible seedlings of *P. indica.* The potential of *M. roridum* as a biological control agent to suppress *P. cinnamomi* in greenhouse potting mixes and in naturally infested field soils was clearly shown. The isolate of *M. roridum* was recovered from the top 10 cm of soil in this particular avocado grove. Similarly, the top layer of decomposing leaf litter was the most suppressive to Phytophthora found in the Ashburner grove at Mt. Tamborine in Queensland according to Cook et al, supra. Although it is unlikely that *M. roridum* is the only cause of suppression in this particular avocado grove, its presence and proven activity against *P. cinnamomi* in various bioassays and greenhouse tests with a highly susceptible host strongly suggest its role in a more complex soil ecosystem.

The wild-type strain TW and the carbendazim-resistant mutant TWm14 both grew well on a basic salt medium with cellulose powder as their only carbon source. The ability to colonize cellulosic material might be a significant factor in permitting these fungi to compete in the soil and colonize the rhizosphere of *P. indica* (Ahmad and Baker, 1987b, supra). The mutant strain TWm14 of *M. roridum* has demonstrated its ability to colonize the rhizosphere of *P. indica.*

It has been demonstrated that pH and temperature can profoundly affect the production of these compounds in culture (Bamburg, supra). It can be assumed that these effects, together with other properties of the soil, could influence the level of antibiotic production. Factors such as rhizosphere-competence and, perhaps, competition for nutrients and space (Baker, "Biological control of plant pathogens: Definitions", pages 25-39, in: *Biological Control in Agriculture IPM Systems,* Hoy et al., eds., Academic Press (1985)); mycoparasitism (Thode, R., supra), and induced resistance (Cook and Baker, "The Nature and Practice of Biological Control of Plant Pathogens", *American Phytopathological Society.* (1983); Dolan et al., "Protection of Persea species against *Phytophthora cinnamomi* and *P. citrocola* by prior inoculation with a citrus isolate of *P. parasitica.*", *Phytopathology* 76:194-198 (1986)) also may be involved in biocontrol of *P. cinnamomi* by *M. roridum.*

Because Phytophthora root rot of avocado is a long-term disease problem, administration of *M. roridum* must be such to enable the Myrothecium to persist as a large, rhizosphere-competent population density on avocado feeder roots over extended periods of time. As stated above, suitable rates of application of strains of *Myrothecium roridum* in a bran or bran-alginate formulation are from about 10 grams/liter of medium to about 50 grams of inoculum/liter of medium, and preferably from about 15 grams of inoculum/liter of medium to about 25 grams of inoculum/liter of medium.

EXAMPLE 3

This example describes a bran-alginate formulation for use as inoculum for biological control of Phytophthora root rot.

Alginate pellets containing fungal preparations of Myrothecium were produced as follows. Wheat bran (Bakers bran, Capitol Milling Co., Los Angeles, Calif.) was ground in a Wiley mill with a 1 mm mesh screen inset. Fifty or 100 g of fine bran was added to 500 or 1000 ml Erlenmeyer flasks and autoclaved for 1 hour. A 5 to 7 day old fungal culture of P4020 (Myrothecium strain TW) obtained as described in Example 1, supra on PDA was flooded with 10-20 ml of water and the conidia removed with a spatula. The conidial suspension was then filtered through three layers of sterile cheese cloth, diluted, added to wheat bran (50 or 100 ml, $1 \times 10^6$ spores/ml), and incubated for 5-7 days at 24° C. in the dark until the bran was colonized by the fungus and the latter started to sporulate. The colonized bran was then homogenized in a glass blender with distilled water (50 g/250 ml). Sodium alginate (Kelgin MV, Kelco, Chicago, Ill.) was dissolved in distilled water (20 g/750 ml, 40° C.) and added to the bran-fungus mixture. The pooled mixture was kept in a 5 liter glass glass beaker in a water bath at 35° C. The mixture was then pumped through a tubing system (8 mm diameter) at high flow rates. Droplets of the bran-alginate mixture were run into 0.25M $CaCl_2$ solution, pH 5.4, to form spherical calcium alginate pellets. The pellets were kept in the $CaCl_2$ solution for 20 min., filtered, thoroughly washed with water, and dried for several days at room temperature (24° C.). The dried alginate pellets were stored in plastic containers either at room temperature or at 5° C. Bran-alginate formulations gave control of Phytophthora root rot equivalent to that achieved with bran alone (Table 8).

TABLE 8

Effect of different Myrothecium spp. grown on wheat bran and introduced into field soil infested with *Phytophthora cinnamoni* on percent root infection *Persea indica*, expressed as number of plants with less or more than 50% root disease. Total of three experiments.

| Treatments[x] | Number of plants with root disease | |
|---|---|---|
| | less than 50% | more than 50% |
| Control | 5 | 40 |
| *Myrothecium roridum* (strain TWm14) | 22 | 23 |
| *M. masonii* (strain P4023) | 23 | 20 |
| *M. roridum* (strain P4053) | 15 | 30 |
| *M. leucotrichum* (strain P4078) | 24 | 21 |
| Alginate pellets (strain TWm14)[y] | 16 | 29 |
| Alginate pellets (strain TWm14)[z] | 26 | 4 |

[x]Fungi grown on wheat bran for 5 days at 24° C. and added to field soil (35 grams/liter, w/v infected with *P. cinnamomi* grown on millet seeds. No bran was used in the control.
[y]Alginate pellets applied to the plants at the first transplant stage (10 to 35 grams/liter, w/v).
[z]Alginate pellets applied to infested field soil (20 grams/liter and 35 grams/liter, w/v).

Thus, a bran-alginate inoculum containing bran colonized by Myrothecium and alginate in a ratio of 4:1 (bran to alginate) is useful to suppress Phytophthora in soil.

Surprisingly, as shown in Table 8, an additional isolate of Myrothecium, *M. masonii,* which displayed no in vitro activity towards Phytophthora was active in tests against root rot on *P. indica* seedlings.

EXAMPLE 4

This example describes the determination of the amount of Myrothecium in an inoculum for biocontrol of Phytophthora.

A bran alginate-formulation containing Myrothecium is prepared as described in Example 3, except that *Myrothecium roridum* strain TWm14 (ATCC No. 20964) is added to the wheat bran.

The pellets of bran-alginate formed as described in Example 3 are disintegrated in a mixture of $8.7 \times 10^{-2}$ molar $KH_2PO_4$ and $3.0 \times 10^{-2}$ molar $Na_2HPO_4$ buffer (pH 7.7) and the cfu/gram of bran-alginate mixture is determined by dilution plating as described by Fravel et al., "Encapsulation of Potential Biocontrol Agents in an Alginate-Clay Matrix" *Phytopathology* 75:774-777 (1985). Dilutions are made on PDA amended with 100 μg carbendazim plus the antibiotics 125 μg of ampicillin, 10 μg rifampicin and 125 μg of chloramphenicol.

This procedure for determining the cfu of Myrothecium present per gram of the bran-alginate mixture may be used to determine the population density of Myrothecium able to suppress a given population density of Phytophthora.

While we have presented embodiments of the invention herein, it is apparent that the basic construction of this invention can be altered to provide still other embodiments without departing from the scope of the claims herein. Therefore, it will be appreciated that the scope of this invention is to be defined by the claims appended hereto rather than by the specific embodiments which have been presented herein by way of example.

We claim:

1. A biologically pure *Myrothecium roridum* strain having ATCC No. 20963.

2. A biologically pure *Myrothecium roridum* strain having ATCC No. 20964.

3. A biologically pure *Myrothecium roridum* strain having ATCC No. 20965.

4. A method for biological control of Phytophthora on plants and in soil, the method comprising adding to soil or plant surfaces containing Phytophthora an inoculum comprising a biologically pure strain of *Myrothecium rodium* selected from the group consisting of ATCC Nos. 20963, 20964 and 20965 and a substrate for carrying said *Myrothecium roridum*.

5. The method of claim 4 wherein said inoculum is added at a rate of from about 10 grams of inoculum per liter of medium to about 50 grams of inoculum per liter of medium to suppress said Phytophthora.

6. The method of claim 4 wherein said inoculum is added at a rate of from about 15 grams of inoculum per liter of medium to about 25 grams of inoculum per liter of medium.

7. The method of claim 5 or 6 wherein said medium is soil or liquid.

8. The method of claim 4 wherein said substrate is bran.

9. The method of claim 4 wherein said substrate comprises a bran-alginate mixture.

10. The method of claim 9 wherein said bran and alginate are present at a ratio of approximately 4:1 bran:alginate by weight.

11. The method of claim 8 or 9 wherein said Myrothecium roridum has been grown on said bran for from about 5 days to about 7 days before use of said inoculum in soil or on plants.

12. The method of claim 4 wherein said inoculum is added to soil to suppress said Phytophthora.

13. The method of claim 4 wherein said inoculum is added to the surface of a plant infected by said Phytophthora.

14. The method of claim 13 wherein the surfaces of said plant area dipped in said inoculum.

15. An inoculum for biocontrol of Phytophthora on plants or in soil comprising a biologically pure strain of *Myrothecium rodium* selected from the group consisting of ATCC Nos. 20963, 20964 and 20965 and a substrate for carrying said *Myrothecium roridum*.

16. The inoculum of claim 15 wherein said substrate is bran or bran-alginate.

17. An inoculum for biocontrol of Phytophthora on plants or in soil comprising bran and a biologically pure strain of *Myrothecium rodium* selected from the group consisting of ATCC Nos. 20963, 20964 and 20965.

18. An inoculum for biocontrol of Phytophthora on plants or in soil comprising bran-alginate and a biologically pure strain of *Myrothecium rodium* selected from the group consisting of ATCC Nos. 20963, 20964 and 20965.

19. The inoculum of claim 17 or 18 wherein said Myrothecium roridum is grown on said bran for from about 5 to about 7 days before use of said inoculum in soil or on plants.

20. The inoculum of claim 17 or 18 wherein said Myrothecium roridum strain has ATCC No. 20964, and said inoculum further comprises a fungicide for reducing the presence of fungi able to complete with said Myrothecium roridum.

21. The inoculum of claim 20 wherein said fungicide is a benzimidazole compound.

22. The inoculum of claim 20 wherein said fungicide is selected from the group consisting of carbendazim, benomyl and thiabendazole.

* * * * *